United States Patent
Ramey et al.

(10) Patent No.: US 8,588,687 B2
(45) Date of Patent: Nov. 19, 2013

(54) COEXISTENCE OF MULTIPLE RADIOS IN A MEDICAL DEVICE

(75) Inventors: Blaine Edward Ramey, Indianapolis, IN (US); Mark Nierzwick, Brownsburg, IN (US); Thomas D. Gurley, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 531 days.

(21) Appl. No.: 12/905,453

(22) Filed: Oct. 15, 2010

(65) Prior Publication Data

US 2012/0095311 A1 Apr. 19, 2012

(51) Int. Cl.
*H04B 7/00* (2006.01)

(52) U.S. Cl.
USPC ............................ 455/41.2; 455/522

(58) Field of Classification Search
USPC ................................ 455/522, 41.2
See application file for complete search history.

(56) References Cited

U.S. PATENT DOCUMENTS

| | | | |
|---|---|---|---|
| 7,340,236 B2 * | 3/2008 | Liang et al. | 455/277.2 |
| 8,114,021 B2 * | 2/2012 | Robertson et al. | 600/300 |
| 2007/0036170 A1 | 2/2007 | Gonikberg et al. | |
| 2008/0300572 A1 | 12/2008 | Rankers et al. | |
| 2008/0312512 A1 | 12/2008 | Brukalo et al. | |
| 2009/0034644 A1 * | 2/2009 | Sandhu | 375/267 |
| 2011/0054282 A1 | 3/2011 | Nekoomaram et al. | |
| 2011/0105026 A1 * | 5/2011 | Hsiao et al. | 455/41.2 |
| 2011/0124996 A1 * | 5/2011 | Reinke et al. | 600/365 |

FOREIGN PATENT DOCUMENTS

| | | |
|---|---|---|
| EP | 1388951 | 2/2004 |
| WO | 2009/137858 | 11/2009 |

OTHER PUBLICATIONS

"Clear Channel Assessment in Energy-constrained Wideband Wireless Networks"; Ramachandran et al.; Jul. 2006.
"A Study of MAC Protocols for WBANs" Ullah et al.; Dec. 2009.
"Ultra-low Power Wireless System On-Chip Solution" Product Specification v1.4; Nordic Semiconductor; Apr. 2010.
"i.MX23 Applications Processor Reference Manual"; Freescale Semiconductor; Nov. 2009.

* cited by examiner

*Primary Examiner* — Ping Hsieh
*Assistant Examiner* — Xin Jia
(74) *Attorney, Agent, or Firm* — Harness, Dickey (57) ABSTRACT

A handheld diabetes management device having a plurality of communication modules for communicating with a plurality of medical devices via a shared antenna or multiple antennas, where the handheld diabetes management device includes a first communication module, a second communication module, and an arbitration module. The first communication module selectively communicates in a first frequency band with an insulin infusion pump external to the handheld diabetes management device via a first antenna using a first wireless communication protocol. The second communication module selectively communicates in the first frequency band with a continuous glucose monitor external to the handheld diabetes management device via a second antenna or the first antenna using a second wireless communication protocol. The arbitration module grants permission to communicate to the first communication module and denies permission to communicate to the second communication module when the first and second communication modules request permission to communicate concurrently.

17 Claims, 9 Drawing Sheets

COEXISTENCE OF MULTIPLE RADIOS IN A MEDICAL DEVICE

FIELD

The present disclosure relates generally to medical devices and more particularly to coexistence of multiple radios in handheld medical devices.

BACKGROUND

Medical devices are often used as diagnostic devices and/or therapeutic devices in diagnosing and/or treating medical conditions of patients. For example, a blood glucose meter is used as a diagnostic device to measure blood glucose levels of patients suffering from diabetes. An insulin infusion pump is used as a therapeutic device to administer insulin to patients suffering from diabetes.

Diabetes mellitus, often referred to as diabetes, is a chronic condition in which a person has elevated blood glucose levels that result from defects in the body's ability to produce and/or use insulin. There are three main types of diabetes. Type 1 diabetes may be autoimmune, genetic, and/or environmental and usually strikes children and young adults. Type 2 diabetes accounts for 90-95% of diabetes cases and is linked to obesity and physical inactivity. Gestational diabetes is a form of glucose intolerance diagnosed during pregnancy and usually resolves spontaneously after delivery.

In 2009, according to the World Health Organization, at least 220 million people worldwide suffer from diabetes. In 2005, an estimated 1.1 million people died from diabetes. The incidence of diabetes is increasing rapidly, and it is estimated that between 2005 and 2030, the number of deaths from diabetes will double. In the United States, nearly 24 million Americans have diabetes, and an estimated 25% of seniors age 60 and older are affected. The Centers for Disease Control and Prevention forecast that 1 in 3 Americans born after 2000 will develop diabetes during their lifetime. The National Diabetes Information Clearinghouse estimates that diabetes costs $132 billion in the United States alone every year. Without treatment, diabetes can lead to severe complications such as heart disease, stroke, blindness, kidney failure, amputations, and death related to pneumonia and flu.

Diabetes is managed primarily by controlling the level of glucose in the bloodstream. This level complex as the level of blood glucose entering the bloodstream is dynamic and complex, and is affected by multiple factors including the amount and type of food consumed, and the amount of insulin (which mediates transport of glucose across cell membranes) in the blood. Variation of insulin in the bloodstream that controls the transport of glucose out of the bloodstream also complicates diabetes management. Blood glucose levels are also sensitive to diet and exercise, but also can be affected by sleep, stress, smoking, travel, illness, menses, and other psychological and lifestyle factors unique to individual patients. The dynamic nature of blood glucose and insulin and all other factors affecting blood glucose often require a person with diabetes to forecast blood glucose levels. Therefore, therapy in the form of insulin, oral medications, or both can be timed to maintain blood glucose levels in an appropriate range.

Management of diabetes is time-consuming for patients because of the need to consistently obtain reliable diagnostic information, follow prescribed therapy, and manage lifestyle on a daily basis. Diagnostic information such as blood glucose is typically obtained from a capillary blood sample with a lancing device and is then measured with a handheld blood glucose meter. Interstitial glucose levels may be obtained from a continuous glucose sensor worn on the body. Prescribed therapies may include insulin, oral medications, or both. Insulin can be delivered with a syringe, an ambulatory infusion pump, or a combination of both. With insulin therapy, determining the amount of insulin to be injected can require forecasting meal composition of fat, carbohydrates, and proteins along with effects of exercise or other physiological states. The management of lifestyle factors such as body weight, diet, and exercise can significantly influence the type and effectiveness of therapy.

Management of diabetes involves large amounts of diagnostic data and prescriptive data acquired in a variety of ways: from medical devices, from personal healthcare devices, from patient-recorded logs, from laboratory tests, and from healthcare professional recommendations. Medical devices include self-monitoring blood glucose (bG) meters (BGMs), continuous glucose monitors (CGMs), ambulatory insulin infusion pumps, diabetes analysis software, and diabetes device configuration software, each of which generates and/or manages large amounts of diagnostic and prescriptive data. Personal healthcare devices include weight scales, blood pressure cuffs, exercise machines, thermometers, and weight management software. Patient recorded logs include information relating to meals, exercise, and lifestyle. Laboratory test results include HbA1C, cholesterol, triglycerides, and glucose tolerance. Healthcare professional recommendations include prescriptions, diets, test plans, and other information relating to the treatment of the patient.

There is a need for a handheld device to aggregate, manipulate, manage, present, and communicate diagnostic data and prescriptive data from medical devices, personal healthcare devices, patient recorded information, biomarker information, and recorded information in an efficient manner. The handheld device can improve the care and health of a person with diabetes so that the person with diabetes can lead a full life and reduce the risk of complications from diabetes.

Additionally, to effectively manage the care and health of the patient, there is a need for the handheld device to communicate with other medical devices and systems. The other medical devices and systems, however, may use different communication protocols and interfaces (e.g., Bluetooth protocol, universal serial bus (USB) interface, etc.). Accordingly, there is a need for the handheld device to include multiple communication protocols and interfaces that enable the handheld device to communicate with the other medical devices and systems in a safe and secure manner. Additionally, to manage coexistence of multiple communication interfaces in the handheld device, there is a need for techniques to decrease probability of collisions and interference between communications performed by the multiple communication interfaces. Further, to minimize the size of the handheld device, two or more communication interfaces may be integrated into a single integrated circuit (IC) and may share an antenna so that additional communication interfaces and corresponding antennas can be added to the handheld device. Sharing an antenna also requires implementing prioritization and arbitration schemes to effectively communicate with the medical devices.

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A handheld diabetes management device having a plurality of communication modules for communicating with a plurality of medical devices via a shared antenna or multiple antennas, where the handheld diabetes management device includes a first communication module, a second communication module, and an arbitration module. The first communication module selectively communicates in a first frequency band with an insulin infusion pump external to the handheld diabetes management device via a first antenna using a first wireless communication protocol. The second communication module selectively communicates in the first frequency band with a continuous glucose monitor external to the handheld diabetes management device via a second antenna or the first antenna using a second wireless communication protocol. The arbitration module grants permission to communicate to the first communication module and denies permission to communicate to the second communication module when the first and second communication modules request permission to communicate concurrently.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

The following description is merely illustrative in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method may be executed in different order without altering the principles of the present disclosure.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Figure 1:
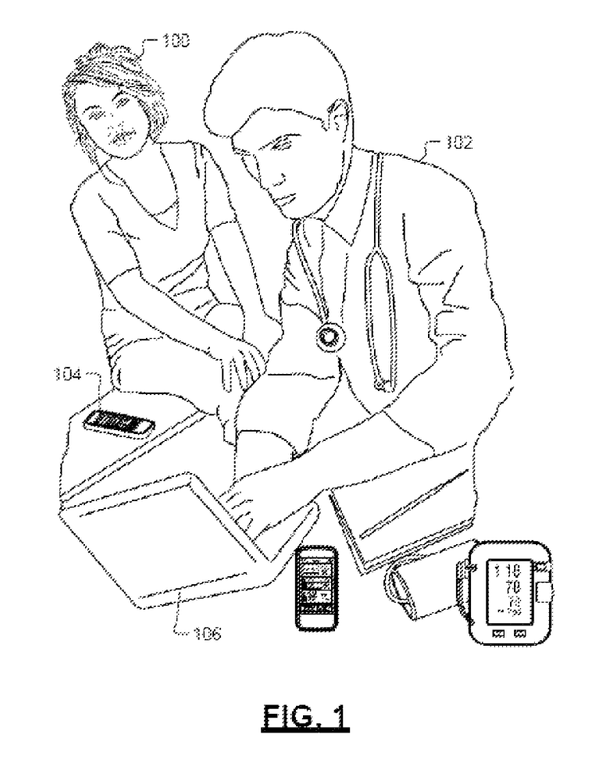
FIG. 1 shows a patient and a treating clinician.

Referring now to FIG. 1, a person 100 with diabetes and a healthcare professional 102 are shown in a clinical environment. Persons with diabetes include persons with metabolic syndrome, pre-diabetes, type 1 diabetics, type 2 diabetics, and gestational diabetics and are collectively referred to as a patient. Healthcare providers for diabetes are diverse and include nurses, nurse practitioners, physicians, and endocrinologists and are collectively referred to as a clinician.

During a healthcare consultation, the patient 100 typically shares with the clinician 102 a variety of patient data including blood glucose measurements, continuous glucose monitor data, amounts of insulin infused, amounts of food and beverages consumed, exercise schedules, and other lifestyle information. The clinician 102 may obtain additional patient data that includes measurements of HbA1C, cholesterol levels, triglycerides, blood pressure, and weight of the patient 100. The patient data can be recorded manually or electronically on a handheld diabetes management device 104, a diabetes analysis software executed on a personal computer (PC) 106, and/or a web-based diabetes analysis site (not shown). The clinician 102 can analyze the patient data manually or electronically using the diabetes analysis software and/or the web-based diabetes analysis site. After analyzing the patient data and reviewing adherence of the patient 100 to previously prescribed therapy, the clinician 102 can decide whether to modify the therapy for the patient 100.

Figure 2:
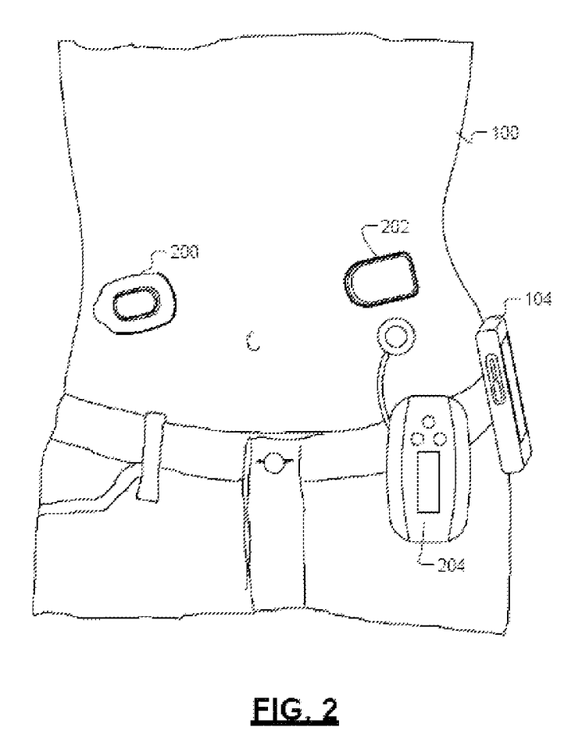
FIG. 2 shows a patient with a continuous glucose monitor (CGM), an ambulatory durable insulin infusion pump, an ambulatory non-durable insulin infusion pump, and a diabetes manger.

Referring now to FIG. 2, the patient 100 can use a continuous glucose monitor (CGM) 200, an ambulatory non-durable insulin infusion pump 202 or an ambulatory durable insulin infusion pump 204 (hereinafter insulin pump 202 or 204), and the handheld diabetes management device 104 (hereinafter the diabetes manager 104). The CGM 200 uses a subcutaneous sensor to sense and monitor the amount of glucose in interstitial fluid of the patient 100 and communicates corresponding data to the diabetes manager 104.

The diabetes manager 104 performs various tasks including measuring and recording blood glucose levels, determining an amount of insulin to be administered to the patient 100 via the insulin pump 202 or 204, receiving patient data via a user interface, archiving the patient data, etc. The diabetes manager 104 periodically receives data from the CGM 200 from which glucose levels of the patient 100 are computed. The diabetes manager 104 transmits instructions to the insulin pump 202 or 204, which delivers insulin to the patient 100. Insulin can be delivered in a scheduled manner in the form of a basal dose, which maintains a predetermined insulin dose to the patient 100. Additionally, insulin can be delivered in the form of a bolus dose, which raises the amount of insulin delivered to the patient 100 by a predetermined amount.

Figure 3:
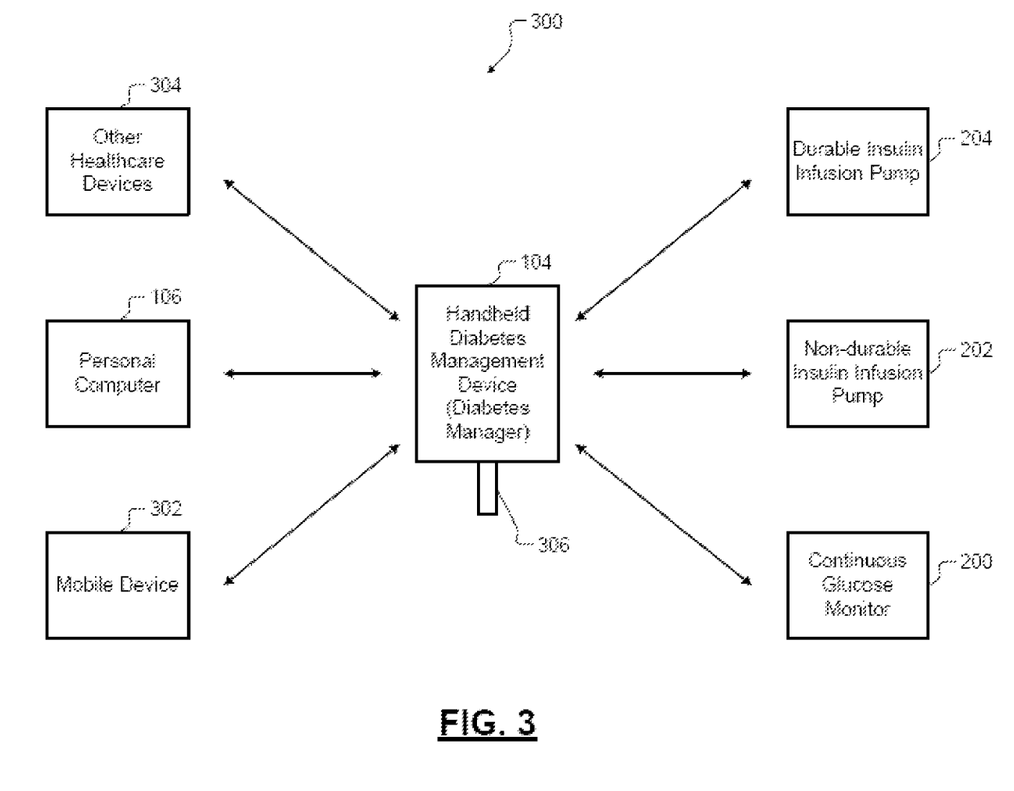
FIG. 3 shows a diabetes management system used by patients and clinicians to manage diabetes.

Referring now to FIG. 3, a diabetes management system 300 used by the patient 100 and the clinician 102 includes one or more of the following devices: the diabetes manager 104, the continuous glucose monitor (CGM) 200, the insulin pump 202 or 204, a mobile device 302, the PC 106 with the diabetes analysis software, and other healthcare devices 304. The diabetes manager 104 is configured as a system hub and communicates with the devices of the diabetes management system 300. Alternatively, the mobile device 302 can serve as the system hub. Communication between the devices in the diabetes management system 300 can be performed using wireless interfaces (e.g., Bluetooth) and/or wireline interfaces (e.g., USB). Communication protocols used by these devices can include protocols compliant with the IEEE 11073 standard as extended using guidelines provided by Continua® Health Alliance Design Guidelines. Further, healthcare records systems such as Microsoft® HealthVault™ and Google™ Health can be used by the patient 100 and clinician 102 to exchange information.

The diabetes manager 104 can receive glucose readings from one or more sources (e.g., from the CGM 200). The CGM 200 continuously monitors the glucose level of the patient 100. The CGM 200 periodically communicates data to the diabetes manager 104 from which the diabetes manager 104 computes glucose levels of the patient. The diabetes manager 104 and the CGM 200 communicate wirelessly using a proprietary wireless protocol. Throughout the present disclosure, Gazell wireless protocol developed by Nordic Semiconductor, Inc. is used as an example only. Any other suitable wireless protocol can be used instead. The Gazell wireless protocol is described in nRF24LE1 Ultra-low Power Wireless System On-Chip Solution, Product Specification v1.4, which is incorporated herein by reference in its entirety.

Additionally, the diabetes manager 104 includes a blood glucose meter (BGM) and a port that communicates with the BGM (not shown). The port can receive a blood glucose measurement strip 306. The patient 100 deposits a sample of blood on the blood glucose measurement strip 306. The BGM analyzes the sample and measures the blood glucose level in the sample. The blood glucose level measured from the sample and/or the glucose level computed using data received from the CGM 200 can be used to determine the amount of insulin to be administered to the patient 100.

The diabetes manager 104 communicates with the insulin pump 202 or 204. The insulin pump 202 or 204 can be configured to receive instructions from the diabetes manager 104 to deliver a predetermined amount of insulin to the patient 100. Additionally, the insulin pump 202 or 204 can receive other information including meal and/or exercise schedules of the patient 100. The insulin pump 202 or 204 can determine the amount of insulin to administer based on the additional information.

The insulin pump 202 or 204 can also communicate data to the diabetes manager 104. The data can include amounts of insulin delivered to the patient 100, corresponding times of delivery, and pump status. The diabetes manager 104 and the insulin pump 202 or 204 can communicate using a wireless communication protocol such as Bluetooth. Other wireless or wireline communication protocols can also be used.

In addition, the diabetes manager 104 can communicate with the other healthcare devices 304. For example, the other healthcare devices 304 can include a blood pressure meter, a weight scale, a pedometer, a fingertip pulse oximeter, a thermometer, etc. The other healthcare devices 304 obtain and communicate personal health information of the patient 100 to the diabetes manager 104 through wireless, USB, or other interfaces. The other healthcare devices 304 may use communication protocols compliant with ISO/IEEE 11073 extended using guidelines from Continual® Health Alliance. The diabetes manager 104 can communicate with the other healthcare devices 304 using interfaces including Bluetooth, USB, etc. Further, the devices of the diabetes management system 300 can communicate with each other via the diabetes manager 104.

The diabetes manager 104 can communicate with the PC 106 using Bluetooth, USB, or other interfaces. A diabetes management software running on the PC 106 includes an analyzer-configurator that stores configuration information of the devices of the diabetes management system 300. The configurator has a database to store configuration information of the diabetes manager 104 and the other devices. The configurator can communicate with users through standard web or computer screens in non-web applications. The configurator transmits user-approved configurations to the devices of the diabetes management system 300. The analyzer retrieves data from the diabetes manager 104, stores the data in a database, and outputs analysis results through standard web pages or computer screens in non-web based applications.

The diabetes manager 104 can communicate with the mobile device 302 using Bluetooth. The mobile device 302 may include a cellular phone, a pager, or a personal digital assistant (PDA). The diabetes manager 104 can send messages to an external network through the mobile device 302. The mobile device 302 can transmit messages to the external network upon receiving requests from the diabetes manager 104.

Figure 4:
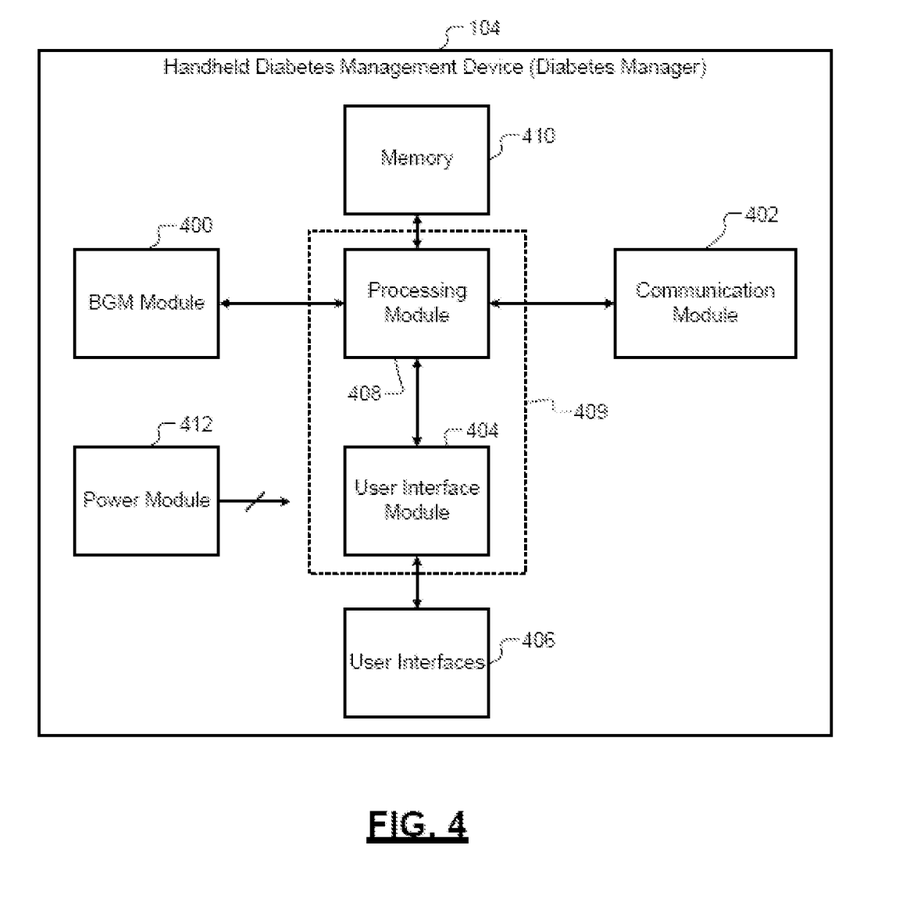
FIG. 4 is a functional block diagram of a diabetes manager.

Referring now to FIG. 4, the diabetes manager 104 comprises a blood glucose measuring (BGM) module 400, a communication module 402, a user interface module 404, user interfaces 406, a processing module 408, memory 410, and a power module 412. The user interface module 404 and the processing module 408 can be implemented by an application processing module 409. The BGM module 400 includes a blood glucose measuring engine that analyzes samples provided by the patient 100 on the blood glucose measurement strip 306 and that measures the amount of blood glucose in the samples. The communication module 402 includes multiple radios that communicate with different devices of the diabetes management system 300. The user interface module 404 interfaces the diabetes manager 104 to various user interfaces 406 that the patient 100 can use to interact with the diabetes manager 104. For example, the user interfaces 406 can include keys, switches, a display, a speaker, a microphone, a secure digital (SD) card port, a USB port, etc. (not shown).

The processing module 408 processes data received from the BGM module 400, the communication module 402, and the user interface module 404. The processing module 408 uses memory 410 for processing and storing data. The memory 410 can include volatile and nonvolatile memory. The processing module 408 outputs data to and receives data from the user interfaces 406 via the user interface module 404. The processing module 408 outputs data to and receives data from the devices of the diabetes management system 300 via the communication module 402. The power module 412 supplies power to the components of the diabetes manager 104. The power module 412 includes a rechargeable battery. The battery can be recharged using an adapter that plugs into a wall outlet. The battery can also be charged via the USB port of the diabetes manager 104.

Figure 5A:
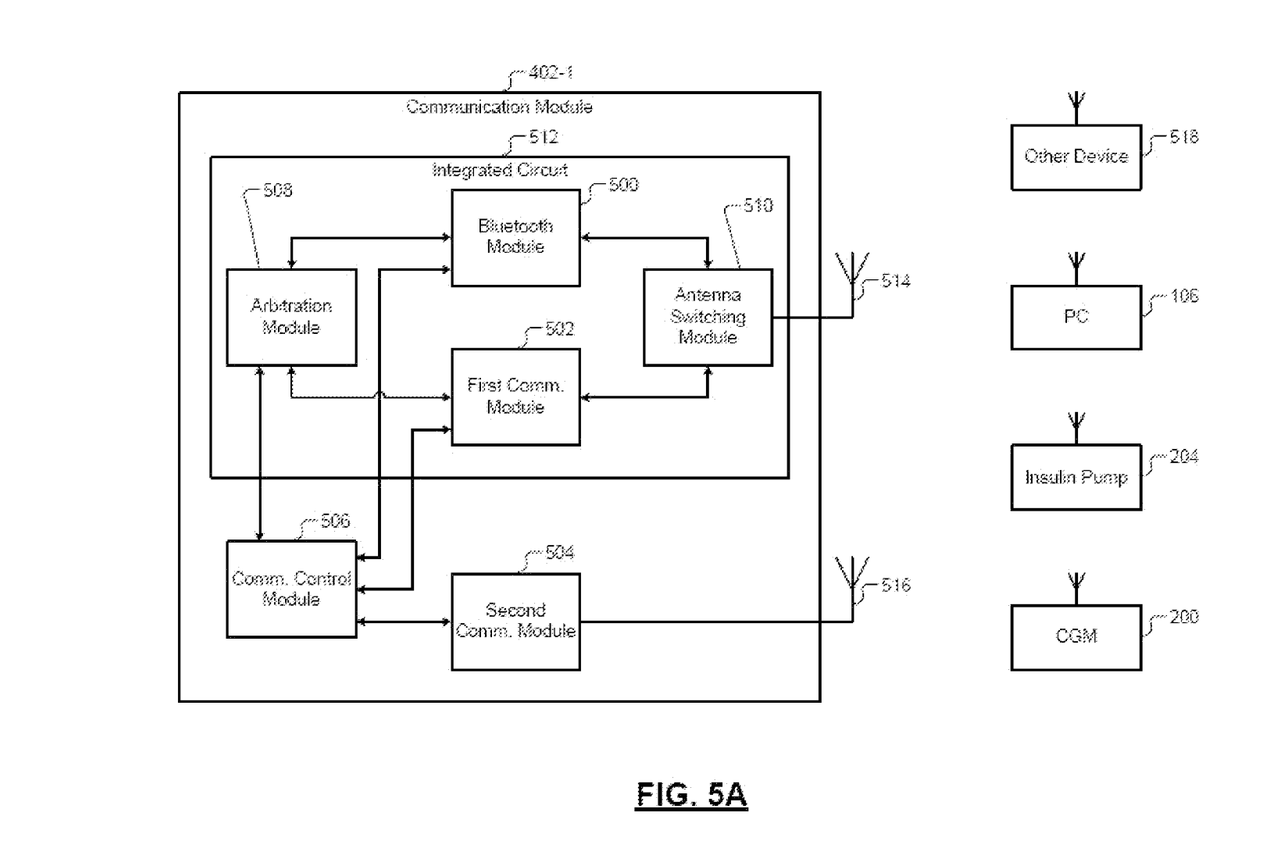
FIG. 5A is a functional block diagram of a communication module used by the diabetes manager of FIG. 4, where the communication module uses a shared antenna.
Figure 5B:
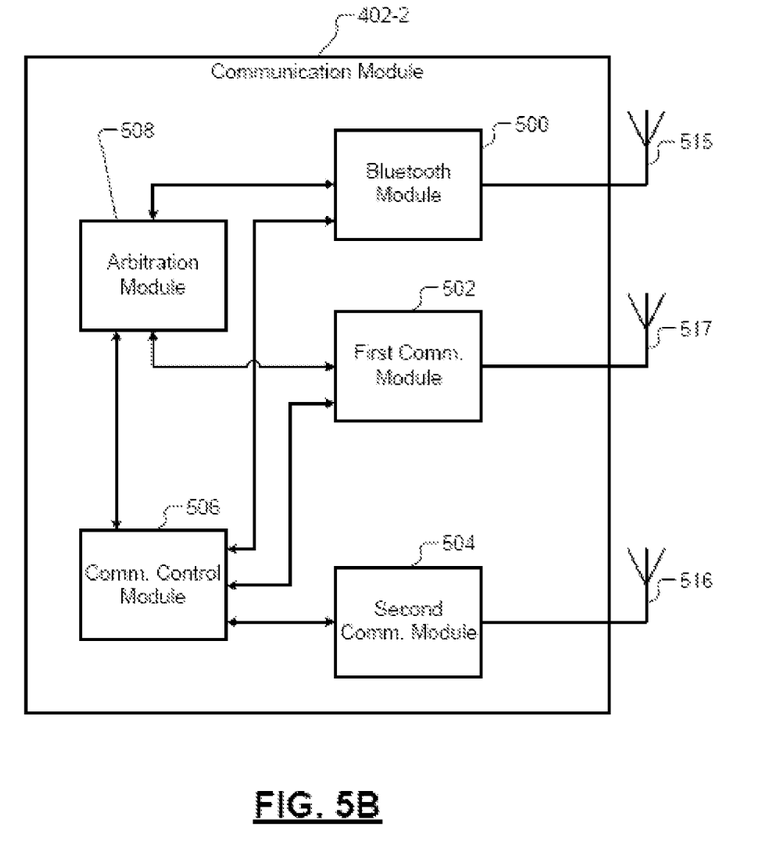
FIG. 5B is a functional block diagram of a communication module used by the diabetes manager of FIG. 4, where the communication module does not use a shared antenna.

Referring now to FIGS. 5A and 5B, different implementations of the communication module 402 are shown. In FIG. 5A, a communication module 402-1 comprises a Bluetooth module 500, a first communication module 502, a second communication module 504, a communication control module 506, an arbitration module 508, and an antenna switching module 510. The Bluetooth module 500 and the first communication module 502 are integrated into an integrated circuit (IC) 512. The Bluetooth module 500 and the first communication module 502 communicate in a 2.4 GHz frequency band (industrial, scientific, and medical or ISM band). The Bluetooth module 500 and the first communication module 502 share a first antenna 514. The second communication module 504 may operate in the same ISM band or in a different frequency band and uses a second antenna 516. The first and second antennas 514 and 516 are spatially orthogonal to reduce interference.

In FIG. 5B, a communication module 402-2 comprises the Bluetooth module 500, the first communication module 502, the second communication module 504, the communication control module 506, and the arbitration module 508. The Bluetooth module 500 and the first communication module 502 are not integrated into an IC. Additionally, the Bluetooth module 500 and the first communication module 502 have separate antennas 515 and 517, respectively. Accordingly, the antenna switching module 510 is unnecessary. The antennas 515, 516, and 517 are spatially orthogonal to reduce interference. The following discussion uses the implementation shown in FIG. 5A as an example only. The teachings disclosed below (except those related to sharing an antenna) apply equally to the implementation shown in FIG. 5B.

In FIG. 5A, the Bluetooth module 500 communicates with the insulin pump 204 and the PC 106. The first communication module 502 communicates with the CGM 200 using the Gazell protocol. The first communication module 502 estimates blood glucose based on the data received from the CGM 200. The second communication module 504 communicates with other device 518 using a wireless communication protocol different than Bluetooth and Gazell protocols. For example, the second communication module 504 may use a communication protocol suitable for communicating with a Medingo insulin pump. Alternatively, the second communication module 504 may use WiFi, Machine-to-Machine cellular, Worldwide Interoperability for Microwave Access (WiMAX), or other wireless or wireline communication protocols developed by IEEE or other entities.

Throughout the present disclosure, the insulin pump 204, the PC 106, and the CGM 200 are used as exemplary devices. Further, the discussion related to priorities of the insulin pump 204, the PC 106, and the CGM 200 is for example only. Additionally or alternatively, the Bluetooth module 500 and the first communication module 502 can communicate with several other devices having different priorities.

Several techniques can be used to manage coexistence of the Bluetooth module 500 and the first communication module 502, which utilize the Bluetooth and Gazell protocols, respectively. For example, the techniques can include application-level control, frequency mapping, and/or hardware control of transceivers used in the Bluetooth module 500 and the first communication module 502. These techniques decrease probability of collisions and interference between communications performed by the Bluetooth module 500 and the first communication module 502. Application-level control includes utilizing the user interfaces 406 to avoid simultaneous communication using the Bluetooth module 500 and the first communication module 502. For example, the patient 100 can utilize the user interfaces 106 to manually select one device to interact with at a time. Frequency mapping includes allocating distinct channels within the ISM band to the Bluetooth module 500 and the first communication module 502. The communication control module 506 performs the frequency mapping as explained below.

Hardware control of transceivers involves using a RF coexistence interface such as BL6450 developed by Texas Instruments that provides RF coexistence signals that can be adapted for use with the Bluetooth module 500 and the first communication module 502. For example, Bluetooth asynchronous connectionless link (ACL) packets and Gazell protocol packets transmitted/received by the Bluetooth module 500 and the first communication module 502 can be interleaved in a controlled manner. The result is an application that appears as communicating via the Bluetooth module 500 and the first communication module 502 simultaneously. The communication control module 506 and the arbitration module 508 control the transceivers of the Bluetooth module 500 and the first communication module 502 as explained below. In addition, the arbitration module 508 can manage the coexistence by automatically arbitrating priority between the Bluetooth module 500 and the first communication module 502 based on various considerations as explained below.

The communication control module 506 controls communication of the diabetes manager 104 with the other devices in the diabetes management system 300 via the Bluetooth module 500 and the first and second communication modules 502 and 504. The arbitration module 508 arbitrates priority between the Bluetooth module 500 and the first communication module 502 when communication via the Bluetooth module 500 and the first communication module 502 is attempted concurrently. The antenna switching module 510 switches the connection of the first antenna 514 between the Bluetooth module 500 and the first communication module 502 depending on whether the Bluetooth module 500 or the first communication module 502 is granted priority.

More specifically, the Bluetooth module 500 selectively communicates in the ISM band with the insulin pump 204 external to the diabetes manager 104 via the first antenna 514 using the Bluetooth protocol. The first communication module 502 selectively communicates in the ISM band with the CGM 200 external to the diabetes manager 104 via the first antenna 514 using the Gazell protocol. To minimize interference and number of packet retries, the communication control module 506 allocates a first channel in the ISM band to the Bluetooth module 500 and allocates a second channel in the ISM band to the first communication module 502. For example, the communication control module 506 can use frequency mapping, where channels allocated to first communication module 502 are removed from Bluetooth channel map. Further, the communication control module 506 reduces interference using techniques including time division multiple access (TDMA), channel hopping, channel adaptation, etc.

The arbitration module 508 arbitrates priority between the Bluetooth module 500 and the first communication module 502 in many ways. For example, the arbitration module 508 typically grants permission to communicate to the Bluetooth module 500 and denies permission to communicate to the first communication module 502 when the Bluetooth module 500 and the first communication module 502 request permission to communicate concurrently. This is because the insulin pump 204 delivers therapy (insulin) to the patient 100 and therefore generally takes precedence over the CGM 200, which collects diagnostic data for estimating glucose level of the patient 100. Additionally, while the diagnostic data can be read from the CGM 200 periodically, scheduled delivery of insulin generally cannot be delayed.

The arbitration module 508 allocates priority differently when a device other than the insulin pump 204 (e.g., the PC 106) is contending with the CGM 200 for priority to communicate with the diabetes manager 104. For example, when the Bluetooth module 500 requests permission to communicate with the PC 106 and the first communication module 502 also requests permission to communicate concurrently, the arbitration module 508 denies permission to communicate to the Bluetooth module 500 and grants permission to communicate to the first communication module 502.

Occasionally, the diagnostic data may indicate that the glucose level of the patient 100 is less than a predetermined threshold, while the insulin pump 204 may be programmed to deliver a bolus insulin dose to the patient 100. In such a situation, communicating the diagnostic data collected by the CGM 200 to the diabetes manager 104 takes precedence over communicating with the insulin pump 204. Accordingly, the arbitration module 508 denies permission to communicate to the Bluetooth module 500 and grants permission to communicate to the first communication module 502 when the Bluetooth module 500 and the first communication module 502 request permission to communicate concurrently.

Stated generally, a handheld medical device (e.g., the diabetes manager 104) comprises a first communication module (e.g., the Bluetooth module 500) that selectively communicates in a first frequency band (e.g., the ISM band) with a first device (e.g., the insulin pump 204) external to the handheld medical device via a first antenna (e.g., 514) using a first wireless communication protocol (e.g., Bluetooth). The first device administers a substance (e.g., insulin) to a patient (100) by communicating with the handheld medical device via the first communication module. A second communication module (e.g., 502) selectively communicates in the first frequency band with a second device (e.g., the CGM 200) external to the handheld medical device via the first antenna using a second wireless communication protocol (e.g., Gazell). The second device monitors a health parameter (e.g., blood glucose level) of the patient by communicating with the handheld medical device via the second communication module. An arbitration module (e.g., 508) grants permission to communicate to the first communication module and denies permission to communicate to the second communication module when the first and second communication modules request permission to communicate concurrently and when the first device has a higher priority than the second device based on a condition of the patient. In some implementations, the first communication module (e.g., the Bluetooth module 500) and the second communication module (e.g., 502) use separate antennas.

Further, the handheld medical device comprises an antenna switching module (e.g., 510) that connects the first antenna to the first communication module when the first communication module is granted permission to communicate and that connects the first antenna to the second communication module when the second communication module is granted permission to communicate. Additionally, the handheld medical device comprises a third communication module (e.g., 504) that selectively communicates in a second frequency band with a third device (e.g., the other device 518) external to the handheld medical device via a second antenna (e.g., 516) using a third wireless communication protocol (e.g., WiFi, WiMAX, etc.) that is different than the first and second wireless communication protocols.

The arbitration module 508 can arbitrate priority based on other events, conditions, and operations of the diabetes manager 104. For example, the arbitration module 508 can deny priority to at least one of the Bluetooth module 500 and the first communication module 502 when the BGM module 400 performs blood glucose measurements. In some implementations, the communication control module 506 may disable communication of the Bluetooth module 500 and the first and second communication modules 502 and 504 when the BGM module 400 performs blood glucose measurements. This is because these communications can cause electrical interference in glucose sensing circuitry of the BGM module 400, which can render the blood glucose measurements inaccurate. Additionally or alternatively, these communications can increase internal temperature of the diabetes manager 104, which can also render the blood glucose measurements inaccurate.

Further, the CGM 200 and/or the insulin pump 204 may generate alarms or alerts to indicate predetermined conditions. For example, the CGM 200 may indicate when glucose level of the patient 100 is less than a predetermined threshold. The insulin pump 204 may indicate when insulin supply in the insulin pump 204 is less than a predetermined threshold, and so on. The arbitration module 508 may grant priority to the communication module corresponding to the device generating the alarm or alert. Occasionally, the patient 100 may press a key on the user interface 406 to send a message via the mobile device 302 indicating an emergency condition. Accordingly, the arbitration module 508 may grant priority to the Bluetooth module 500 to communicate with the mobile device 302.

Additionally, the arbitration module 508 may grant or deny priority based on a state of charge of the battery. For example, when the state of charge is less than a predetermined threshold, the arbitration module 508 may grant priority to the Bluetooth communication module 500 to communicate with the insulin pump 204 and may deny priority to the first communication module 502, which communicates with the CGM 200.

The arbitration module 508 can also arbitrate priority based on the direction of communication between the diabetes manager 104 and the insulin pump 204, the CGM 200, and the PC 106. For example, when the arbitration module 508 receives signals from the Bluetooth module 500 and the first communication module 502 for concurrent communication, the arbitration module 508 identifies the insulin pump 204, the PC 106, or the CGM 200 as the source or destination of the signals. Depending on the operation being performed, the arbitration module 508 determines whether the insulin pump 204, the PC 106, or the CGM 200 has a higher priority and grants permission to communicate to the corresponding communication module. For example, when the diabetes manager 104 receives configuration or other updates (e.g., firmware updates) from the PC 106, the arbitration module 508 grants priority to the Bluetooth module 500 and denies priority to the first communication module 502.

Figure 6:
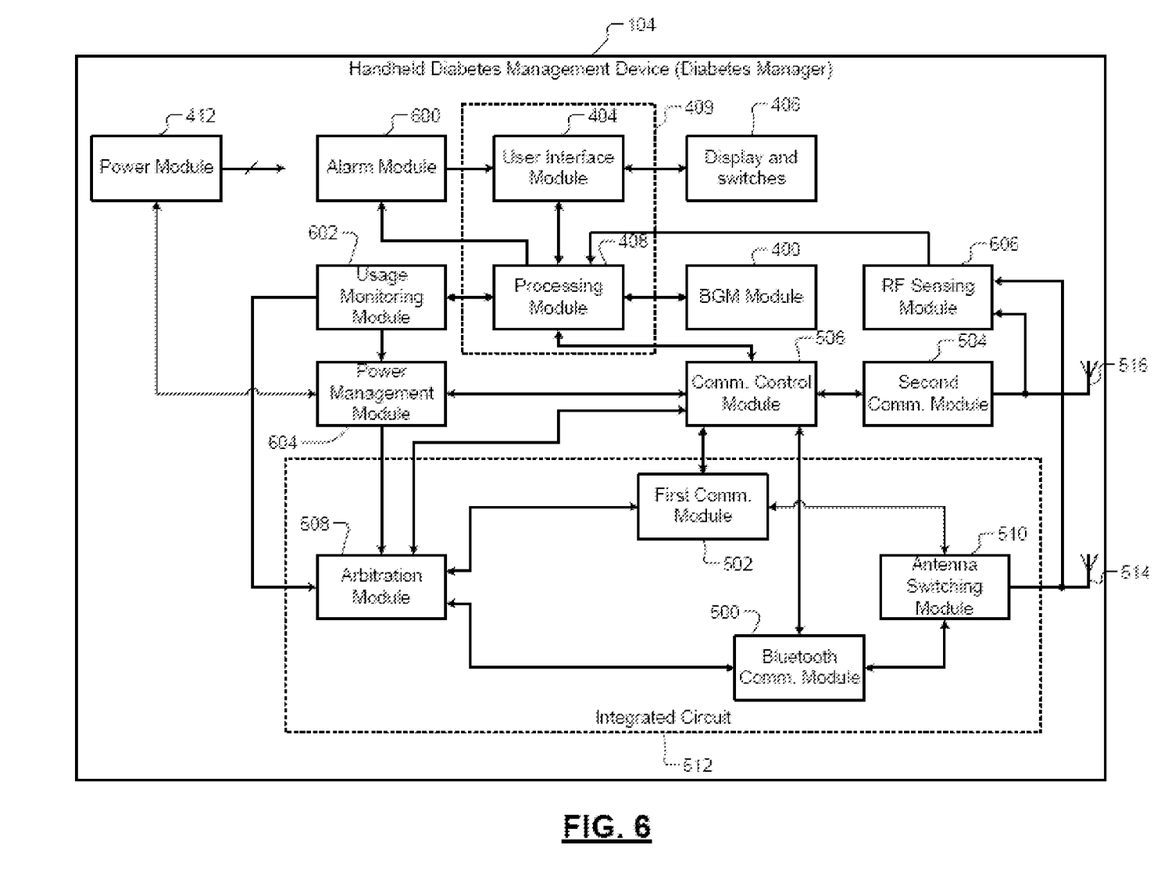
FIG. 6 is a detailed functional block diagram of the diabetes manager of FIG. 4.

Referring now to FIG. 6, a detailed functional block diagram of the diabetes manager 104 is shown. Although the Bluetooth module 500 and the first communication module 502 are shown integrated and sharing the antenna 514, the Bluetooth module 500 and the first communication module 502 need to not be integrated and can have separate antennas as shown in FIG. 5B. Elements of the diabetes manager 104 that are described above are not described again. In addition to these elements, the diabetes manager 104 includes an alarm module 600, a usage monitoring module 602, a power management module 604, and a radio frequency (RF) sensing module 606.

The alarm module 600 outputs alarm signals (e.g., audio, video, vibrate, and/or other signals) to the user interfaces 406 (e.g., when blood glucose level is less than a first predetermined threshold or greater than a second predetermined threshold). The usage monitoring module 602 monitors usage of the diabetes manager 104. For example, the usage monitoring module 602 detects when the diabetes manager 104 is idle, generating an alarm, measuring blood glucose level, or communicating with the PC 106, the insulin pump 204, the CGM 200, and so on.

The power management module 604 monitors the amount of power available from the battery. Based on the usage of the diabetes manager 104 and the power available from the battery, the power management module 604 deactivates one or more components of the diabetes manager 104 to save power. Deactivation of a component includes supplying no power to the component (i.e., shutting down the component) or supplying minimum power to put the component in a standby or power save mode (e.g., turning off or slowing one or more clocks used by the component).

Based on the usage and the power available, the arbitration module 508 arbitrates priority between the Bluetooth module 500 and the first communication module 502. For example, when the power available is less than a predetermined threshold, the arbitration module 508 can deny permission to the communication module that will consume more power and grant priority to the communication module that will consume less power.

When the BGM module 400 measures blood glucose level in the blood sample, the power management module 604 deactivates at least one or all of the Bluetooth module 500 and the first and second communication modules 502 and 504. The RF sensing module 606 senses RF signals in the proximity of the diabetes manager 104. For example, the RF sensing module 606 uses techniques such as clear channel assessment (CCA), which is generally used to find a best channel for transmission, to sense RF signals. Specifically, rather than using CCA to find the best channel for transmission, the RF sensing module 606 uses CCA to detect RF emitting devices in the vicinity of the diabetes manager 104. The processing module 408 deactivates the BGM module 400 when the RF sensing module 606 senses the RF signals proximate to the diabetes manager 104 to avoid interference with the blood glucose measurement.

In some implementations, the RF sensing module 606 can be implemented in transceivers of the Bluetooth module 500 and the first and second communication modules 502 and 504. For example, the transceivers include radio signal strength indicator (RSSI) circuitry that determines an amount of power needed to maintain a communications link with a device. The RSSI circuitry of the transceivers can be used to scan the respective frequency bands to detect RF signals proximate to the diabetes manager 104.

Figure 7:
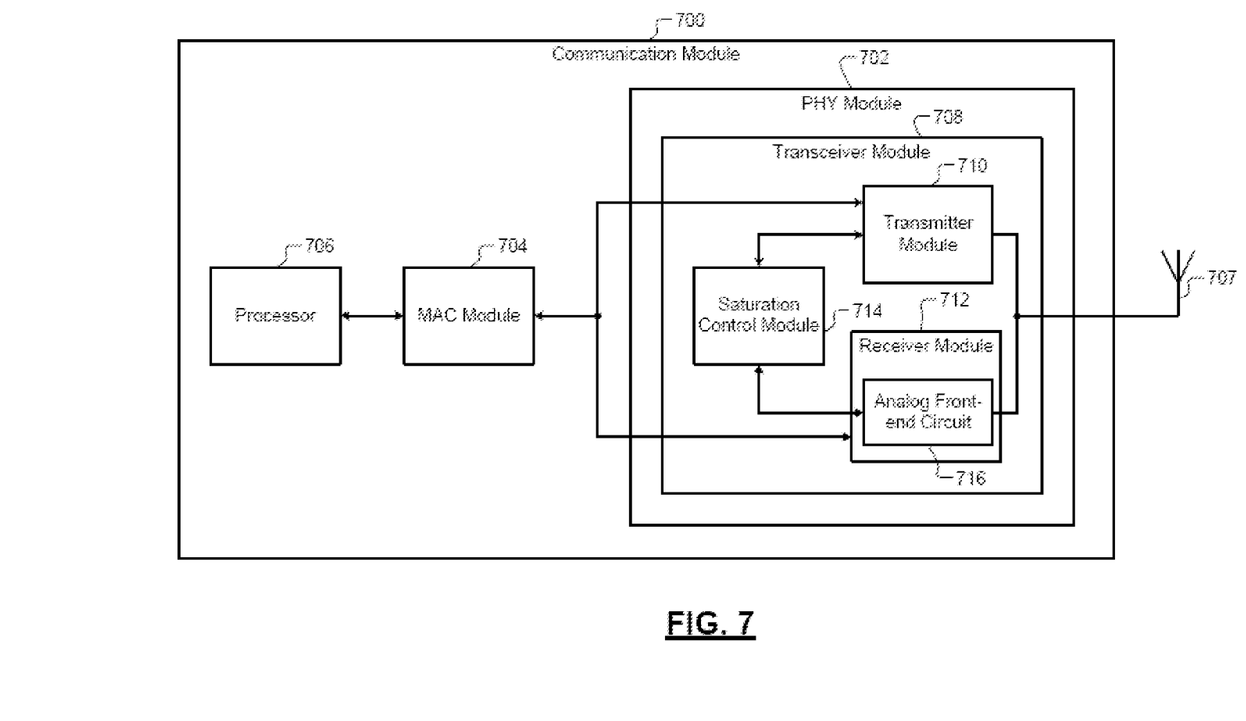
FIG. 7 is a functional block diagram of a communication module.

Referring now to FIG. 7, a functional block diagram of a communication module 700 is shown. The communication module 700 is representative of the Bluetooth module 500 or the first or second communication module 502 or 504. The communication module 700 comprises a physical layer (PHY) module 702, a media access control (MAC) module 704, a processor module 706, and an antenna 707. The PHY module 702 comprises a transceiver module 708, which includes a transmitter module 710, a receiver module 712, and a saturation control module 714. The transmitter module 710 is collocated with the receiver module 712. The transmitter module 710 and the receiver module 712 transmit and receive data via the antenna 707, respectively. For example, for the first communication module 502, the transceiver module 708 may include an nRF24LE1 transceiver developed by Nordic Semiconductor, Inc. described in the nRF24LE1 Ultra-low Power Wireless System On-Chip Solution, Product Specification v1.4, which is incorporated herein by reference in its entirety.

The MAC module 704 communicates with the transmitter module 710 and the receiver module 712 and controls access of the communication module 700 to the wireless medium. The processor module 706 processes data transmitted and received by the transmitter module 710 and the receiver module 712, respectively. The receiver module 712 includes a front-end circuit 716 that performs functions including demodulation, analog-to-digital conversion (ADC), automatic gain control (AGC), etc. The saturation control module 714 prevents saturation of the front-end circuit 716 by the transmitter module 710 to minimize interference. In some implementations, the AGC in the front-end circuit 716 can prevent saturation of the front-end circuit 716 so long as signal strengths of received signals are less than a predetermined threshold.

Figure 8:
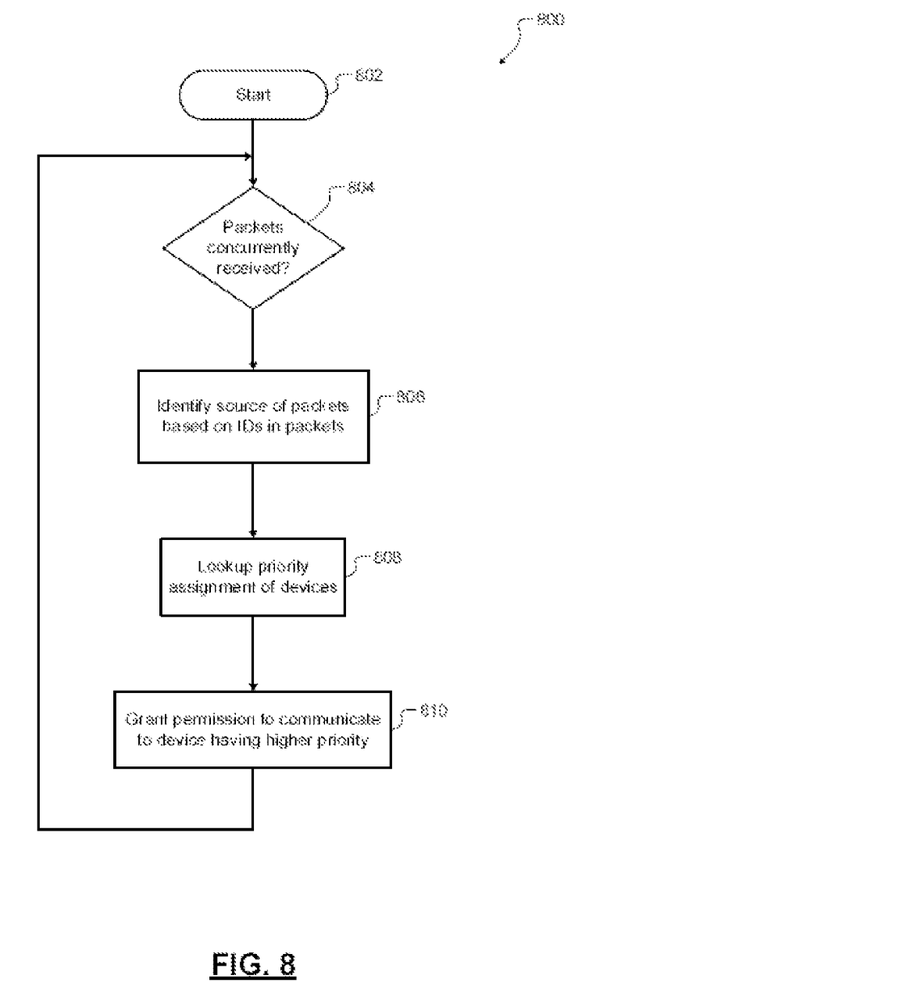
FIG. 8 is a flowchart of a method for arbitrating priority between a plurality of communication modules using a shared antenna.

Referring now to FIG. 8, in an exemplary implementation, the arbitration module 508 performs a method 800 for arbitrating priority between the Bluetooth module 500 and the first communication module 502. Control begins at 802. At 804, control determines if requests for simultaneous communication are received from the Bluetooth module 500 and the first communication module 502. For example, packets may be simultaneously received via the first and second antennas 514 and 516. If the result at 804 is false, control waits. If the result at 804 is true, at 806, control identifies devices that originated the packets based on identifying information included in the packets.

At 808, control looks up predetermined priorities for the identified devices. For example, the predetermined priorities may be stored in a lookup table or control registers in the arbitration module 508. The predetermined priorities can be altered/updated dynamically based on the usage and operation of the diabetes manager 104 and associated devices described above. At 810, based on the priority assigned to the identified devices, control grants permission to communicate to the device having higher priority. Control returns to 802.

In an exemplary embodiment, the arbitration module 508 arbitrates priority between the Bluetooth module 500 and the first communication module 502 using coexistence signals as follows. For managing coexistence, the Bluetooth module 500 of FIG. 5 utilizes three coexistence signals: BT_RF_ACTIVE, BT_PRIORITY, and BT_TX_CONFX. The Bluetooth module 500 outputs BT_RF_ACTIVE to indicate transmit or receive activity of the Bluetooth module 500. The Bluetooth module 500 outputs BT_PRIORITY to indicate that a priority transaction is about to occur and whether the activity is transmit or receive type. BT_TX_CONFX is an input to the Bluetooth module 500 that disables an internal power amplifier of the Bluetooth module 500 when asserted.

The first communication module 502 utilizing the nRF24LE1 transceiver does not inherently include hardware to implement the co-existence signals. Similar operations, however, can be performed by the first communication module 502 using the arbitration module 508 and/or the communication control module 506. For example, when the first communication module 502 is about to receive diagnostic data from the CGM 200, the arbitration module 508 and/or the communication control module 506 can assert BT_TX- _CONFX, check BT_RF_ACTIVE to ensure that the Bluetooth module 500 is no longer active, and allow the first communication module 502 to receive the diagnostic data from the CGM 200. After the transaction between first communication module 502 and the CGM 200 is completed, the arbitration module 508 and/or the communication control module 506 can de-assert BT_TX_CONFX. An exemplary method for managing coexistence using this approach performed by the arbitration module 508 and/or the communication control module 506 is explained below.

Figure 9:
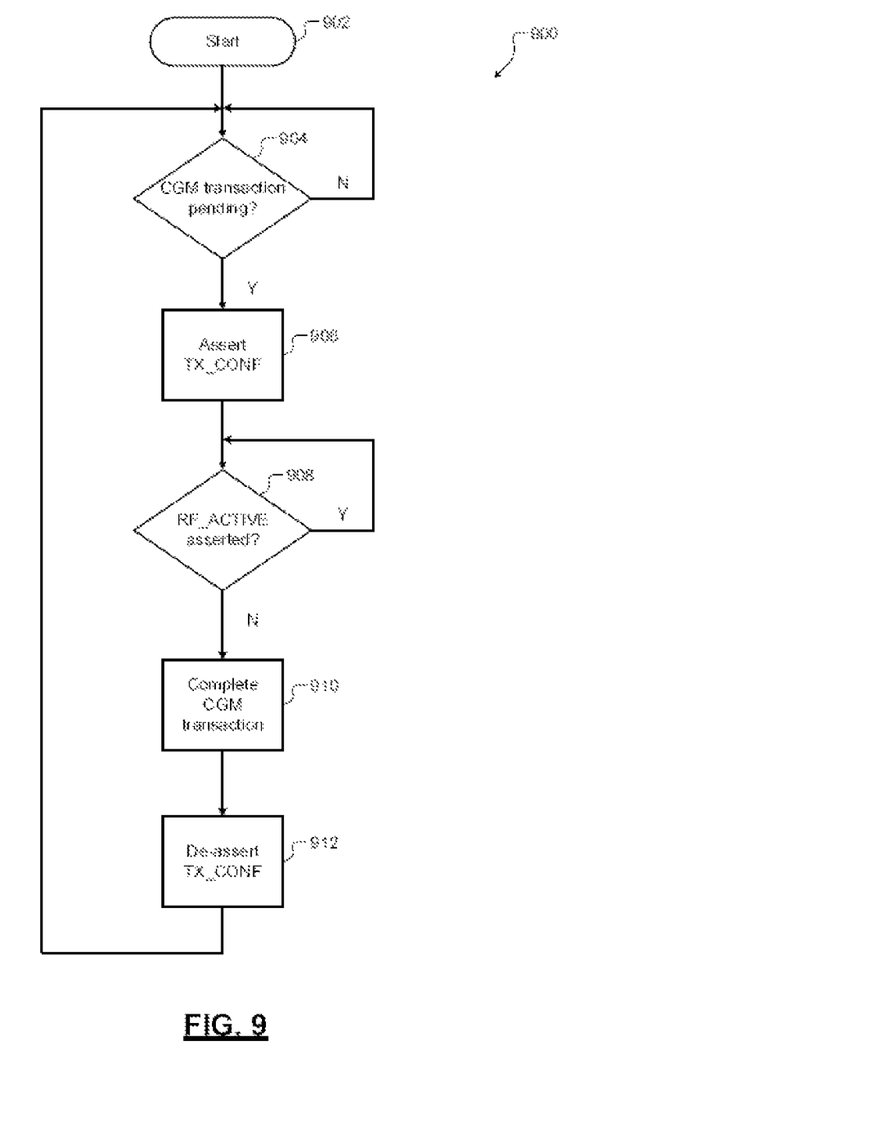
FIG. 9 is a flowchart of a method for managing coexistence of a plurality of communication modules using a shared antenna.

Referring now to FIG. 9, a flowchart of a method 900 for managing coexistence of the Bluetooth module 500 and the first communication module 502 using a shared antenna is shown. Control begins at 902. At 904, control determines if a transaction with CGM 200 using the first communication module 502 is pending. Control waits if a transaction is not pending. At 906, if a transaction is pending, control asserts BT_TX_CONF, which disables an internal power amplifier of the Bluetooth module 500. At 908, control determines if BT_RF_ACTIVE is asserted, which indicates transmit or receive activity of the Bluetooth module 500. Control returns to 908 if BT_RF_ACTIVE is asserted. At 910, if BT_RF_ACTIVE is not asserted, which indicates no transmit or receive activity by the Bluetooth module 500, control completes the pending transaction using the first communication module 502. At 912, control de-asserts BT_TX_CONF, which enables an internal power amplifier of the Bluetooth module 500, and control returns to 902.

When large amounts of diagnostic data are downloaded from the CGM 200 using the first communication module 502, the RF usage may have large gaps where the Bluetooth module 500 can have an opportunity to send and receive packets. For example, a largest Gazell packet may be 1.316 msec long. Accordingly, even if 10 records were downloaded at a time, for example, including acknowledgements, the Bluetooth module 500 may be disabled on the order of 15 to 30 msec depending on the number of retries and other timing parameters.

Further, when a large number of records are to be downloaded from the CGM 200, the number of records can be divided into groups with a gap of 50 to 100 msec between the groups due to other system constraints. The quality of service (QoS) of the Bluetooth module 500 is set to reliable so that Bluetooth packets are retried until Bluetooth link breaks down, which makes the Bluetooth interface robust. The default link timeout for the Bluetooth interface is typically 20 seconds while applications generally have a much shorter timeout such as 1 second.

A sniff interval setting of the Bluetooth module 500 can impact this strategy. While Bluetooth is a polling-based system, the connection between the diabetes manager 104 and the insulin pump 204 can use sniff mode to save power. The sniff interval can be set to 16 msec, for example, which means that the slave and host devices (e.g., the insulin pump 204 and the Bluetooth module 500) can wake up to exchange packets every 16 msec.

In summary, if the first communication module 502 allows the Bluetooth module 500 to complete transactions and does not disable the Bluetooth module 500 for an extended period of time, an RF coexistence interface such as BL6450 provided by Texas Instruments can be used to manage coexistence of the Bluetooth module 500 and the first communication module 502.

The broad teachings of the disclosure can be implemented in a variety of forms. Therefore, while this disclosure includes particular examples, the scope of the disclosure should not be so limited since other modifications will become apparent to the skilled practitioner upon a study of the drawings, the specification, and the following claims.

What is claimed is:

1. A handheld diabetes management device that arbitrates priority among multiple communication modules having a shared antenna for communicating with a plurality of medical devices, the handheld diabetes management device comprising:
   a blood glucose measuring module that selectively measures blood glucose in a blood sample;
   a first communication module that selectively communicates in a first frequency band with an insulin infusion pump external to the handheld diabetes management device via a first antenna using a first wireless communication protocol;
   a second communication module that selectively communicates in the first frequency band with a continuous glucose monitor external to the handheld diabetes management device via the first antenna using a second wireless communication protocol; and
   an arbitration module that
   receives signals from the first and second communication modules for concurrent communication with the insulin infusion pump and the continuous glucose monitor, respectively,
   identifies the insulin infusion pump and the continuous glucose monitor as the source or destination of the signals,
   determines that the insulin infusion pump has a higher priority than the continuous glucose monitor, and
   grants permission to communicate to the first communication module, and
   denies permission to communicate to the second communication module; and
   a power management module that deactivates the first and second communication modules while the blood glucose measuring module measures the blood glucose in the blood sample.

2. The handheld diabetes management device of claim 1 further comprising:
   a radio frequency (RF) sensing module that selectively senses RF signals; and
   a processing module that deactivates the blood glucose measuring module when the RF sensing module senses the RF signals proximate to the handheld diabetes management device.

3. The handheld diabetes management device of claim 1 further comprising:
   a third communication module that selectively communicates in a second frequency band with a device external to the handheld diabetes management device via a second antenna using a third wireless communication protocol that is different than the first and second wireless communication protocols,
   wherein the second frequency band is different than the first frequency band,
   wherein the device is different than the insulin infusion pump and the continuous glucose monitor, and
   wherein the first and second antennas are orthogonal.

4. The handheld diabetes management device of claim 1 further comprising a communication control module that allocates a first channel set in the first frequency band to the first communication module and that allocates a second channel set in the first frequency band to the second communication module.

5. The handheld diabetes management device of claim 1 further comprising an antenna switching module that connects the first antenna to the first communication module when the first communication module is granted permission to communicate and that connects the first antenna to the second communication module when the second communication module is granted permission to communicate.

6. The handheld diabetes management device of claim 1 further comprising a communication control module that
 detects when a communication of the second communication module is pending,
 disables a power amplifier of the first communication module,
 confirms that the first communication module has stopped communication,
 allows the second communication module to complete the communication, and
 enables the power amplifier of the first communication module.

7. A handheld medical device that arbitrates priority among multiple communication modules having a shared antenna for communicating with a plurality of medical devices, the handheld medical device comprising:
 a blood glucose measuring module that selectively measures blood glucose in a blood sample;
 a first communication module that selectively communicates in a first frequency band with a first device external to the handheld medical device via a first antenna using a first wireless communication protocol, wherein the first device administers a substance to a patient by communicating with the handheld medical device via the first communication module,
 a second communication module that selectively communicates in the first frequency band with a second device external to the handheld medical device via the first antenna using a second wireless communication protocol, wherein the second device monitors a health parameter of the patient by communicating with the handheld medical device via the second communication module;
 an arbitration module that grants permission to communicate to the first communication module and that denies permission to communicate to the second communication module when the first and second communication modules request permission to communicate concurrently and when the first device has a higher priority than the second device based on a condition of the patient;
 a radio frequency (RF) sensing module that selectively senses RF signals; and
 a processing module that deactivates the blood glucose measuring module when the RF sensing module senses the RF signals proximate to the handheld medical device.

8. The handheld medical device of claim 7 further comprising:
 a power management module that deactivates the first and second communication modules when the blood glucose measuring module measures the blood glucose in the blood sample.

9. The handheld medical device of claim 7 further comprising:
 a third communication module that selectively communicates in a second frequency band with a third device external to the handheld medical device via a second antenna using a third wireless communication protocol that is different than the first and second wireless communication protocols,
 wherein the second frequency band is different than the first frequency band, and
 wherein the first and second antennas are orthogonal to reduce near-field interference.

10. The handheld medical device of claim 7 further comprising a communication control module that allocates a first channel set in the first frequency band to the first communication module and that allocates a second channel set in the first frequency band to the second communication module.

11. The handheld medical device of claim 7 further comprising an antenna switching module that connects the first antenna to the first communication module when the first communication module is granted permission to communicate and that connects the first antenna to the second communication module when the second communication module is granted permission to communicate.

12. The handheld medical device of claim 7 further comprising a communication control module that
 detects when a communication of the second communication module is pending,
 disables a power amplifier of the first communication module,
 confirms that the first communication module has stopped communication,
 allows the second communication module to complete the communication, and
 enables the power amplifier of the first communication module.

13. A handheld diabetes management device that arbitrates priority among multiple communication modules having a shared antenna for communicating with a plurality of medical devices, the handheld diabetes management device comprising:
 a blood glucose measuring module that selectively measures blood glucose in a blood sample;
 a first communication module that selectively communicates in a first frequency band with an insulin infusion pump external to the handheld diabetes management device via a first antenna using a first wireless communication protocol, wherein the insulin infusion pump selectively receives an instruction from the handheld diabetes management device to administer insulin to a patient;
 a second communication module that selectively communicates in the first frequency band with a continuous glucose monitor external to the handheld diabetes management device via the first antenna using a second wireless communication protocol, wherein the continuous glucose monitor selectively communicates a glucose level of the patient to the handheld diabetes management device;
 an arbitration module that denies permission to communicate to the first communication module and that grants permission to communicate to the second communication module when the first and second communication modules request permission to communicate concurrently and when the blood glucose level of the patient is less than a threshold;
 a power management module that deactivates the first and second communication modules when the blood glucose measuring module measures the blood glucose in the blood sample;
 a radio frequency (RF) sensing module that selectively senses RF signals; and
 a processing module that deactivates the blood glucose measuring module when the RF sensing module senses the RF signals proximate to the handheld diabetes management device.

14. The handheld diabetes management device of claim 13 further comprising:
- a third communication module that selectively communicates in a second frequency band with a device external to the handheld diabetes management device via a second antenna using a third wireless communication protocol that is different than the first and second wireless communication protocols,
- wherein the second frequency band is different than the first frequency band,
- wherein the device is different than the insulin infusion pump and the continuous glucose monitor, and
- wherein the first and second antennas are orthogonal.

15. The handheld diabetes management device of claim 13 further comprising a communication control module that allocates a first channel set in the first frequency band to the first communication module and that allocates a second channel set in the first frequency band to the second communication module.

16. The handheld diabetes management device of claim 13 further comprising an antenna switching module that connects the first antenna to the first communication module when the first communication module is granted permission to communicate and that connects the first antenna to the second communication module when the second communication module is granted permission to communicate.

17. The handheld diabetes management device of claim 13 further comprising a communication control module that
- detects when a communication of the second communication module is pending,
- disables a power amplifier of the first communication module,
- confirms that the first communication module has stopped communication,
- allows the second communication module to complete the communication, and
- enables the power amplifier of the first communication module.

* * * * *